(12) United States Patent
Song et al.

(10) Patent No.: US 7,407,789 B2
(45) Date of Patent: Aug. 5, 2008

(54) RECOMBINANT STAPHYLOKINASE DERIVATIVES AND THE PREPARATION AND APPLICATIONS THEREOF

(75) Inventors: Houyan Song, Shanghai (CN); Gang Song, Shanghai (CN)

(73) Assignee: Fudan University, Shanghai (CN)

( * ) Notice: Subject to any disclaimer, the term of this patent is extended or adjusted under 35 U.S.C. 154(b) by 465 days.

(21) Appl. No.: 10/182,160

(22) PCT Filed: Jan. 23, 2001

(86) PCT No.: PCT/CN01/00102

§ 371 (c)(1),
(2), (4) Date: Jan. 22, 2003

(87) PCT Pub. No.: WO01/55359

PCT Pub. Date: Aug. 2, 2001

(65) Prior Publication Data

US 2005/0202000 A1    Sep. 15, 2005

(30) Foreign Application Priority Data

Jan. 28, 2000  (CN) ............................... 00 1 11627

(51) Int. Cl.
*C12N 9/52* (2006.01)
*C12N 9/00* (2006.01)
*C12N 9/24* (2006.01)
*C12N 9/48* (2006.01)
*C12N 9/50* (2006.01)
*C12N 15/00* (2006.01)
*A61K 38/48* (2006.01)
*A61K 39/085* (2006.01)
*A61K 39/02* (2006.01)
*A61K 38/00* (2006.01)
*C07K 1/00* (2006.01)

(52) U.S. Cl. ..................... 435/220; 435/183; 435/200; 435/212; 435/219; 435/320.1; 424/94.64; 424/243.1; 424/190.1; 530/300; 530/350

(58) Field of Classification Search ................ 530/300, 530/350; 424/96.64, 243.1, 190.1; 435/172.1, 435/183, 200, 212, 219, 220, 320.1
See application file for complete search history.

(56) References Cited

U.S. PATENT DOCUMENTS 6,383,483 B1 * 5/2002 Collen ..................... 424/94.64

OTHER PUBLICATIONS

Bowie et al (Science, 1990, 257:1306-1310).*
Thomas E. Creighton, in his book, "Proteins: Structures and Molecular Properties, 1984", (pp. 314-315).*
Creighton, in his book Protein Structure: A Practical Approach, 1989; pp. 184-186.*

GenBank, GI:47425, Mar. 30, 1995—Nucleotide sequence of the staphylokinase gene from *Staphylococcus aureus*, T. Sako and N. Tsuchida.

Granelli-Piperno et al, A study of proteases and protease-inhibitor complexes in biological fluids Journal of Experimental Medicine, Jul. 1978, vol. 148, pp. 223-234.

Lijnen et al, On the mechanism of fibrin-specific plasminogen activation by staphylokinase, Journal of Biological Chemistry, Jun. 1991, vol. 266 pp. 11826-11832.

Nichols et al, Development of GPIIb/IIIa antagonists as antithrombotic drugs, Trends in Pharmacological Science, Nov. 1992, vol. 13 pp. 413-417.

Frishman et al, Novel antiplatelet therapies for treatment of patients with ischemic heart disease: inhibitors of the platelet glycoprotein IIb/IIIa integrin receptor, American Heart Journal, Oct. 1995, vol. 130 pp. 877-892.

Declerck et al, Prevalence and induction of circulating antibodies against recombinant staphylokinase, Thrombosis and Haemostasis, Jan. 1994, vol. 71, pp. 129-133.

Verstraete et al, Novel antithrombotic drugs in development, Drugs, Jun. 1995 vol. 49, pp. 856-884.

Silence et al, Structure-function relationships in staphylokinase as revealed by "clustered charge to alanine" mutagenesis Journal of Biological Chemistry, Nov. 1995, vol. 270, pp. 27192-27198.

Smith et al Protein loop grafting to construct a variant of tissue-type plasminogen activator that binds platelet integrin alpha IIb beta 3, Journal of Biological Chemistry, Dec. 1995, vol. 270, pp. 30486-30490.

(Continued)

*Primary Examiner*—Robert A. Zeman
*Assistant Examiner*—Lakia J Tongue
(74) *Attorney, Agent, or Firm*—Cook, Alex, McFarron, Manzo, Cummings & Mehler, Ltd.

(57) ABSTRACT

The present invention relates to the biotechnology field, more particularly, to novel recombinant staphylokinase (RGD/KGD-Sak) derivatives and the preparation thereof. The derivatives, have a low polymerizing ability, low immunogenicity and a bifunctionality of thrombolytics and anticoagulant. Based on the trimensional structural analysis of the monomer and dimer of recombinant staphylokinases and their biochemical properties, we designed two novel bifunctional staphylokinase molecular structures. Mutant genes were constructed by PCR site-directed mutagenesis, which were then recombined with a prokaryotic vector and used to transform *E. coli*. Engineered strains with a high expression level were selected by screening and propagated by fermentation, followed by disruption of the cells, centrifugation to collect inclusion bodies, renaturation, and purification of RGD/KGD-SAK through a two-step method. After lyophilized, the polymerizing ability and immunogenicity of the products decreased significantly. The derivatives can not only activate fibrinogen to lyse thrombus, but also significantly inhibit the platelet aggregation induced by ADP, suggesting that they have the bifunctionality of thrombolytics and anticoagulant.

4 Claims, 2 Drawing Sheets

OTHER PUBLICATIONS

Li et al. Minimization of a polypeptide hormone, Science, Dec. 1995, vol. 270 pp. 1657-1660.

Zhan et al Crystallization and preliminary X-ray diffraction studies of recombinant staphylokinase, Acta Crystallogr D Biol Crystallogr., May 1996, vol. 52, pp. 564-565.

Rabijns et al Three-dimensional structure of staphylokinase, a plasminogen activator with therapeutic potential Nature Structural Biology, May 1997, vol. 4, pp. 357-360.

Collen, Staphylokinase: a potent, uniquely fibrin-selective thrombolytic agent Nat Med Mar. 1998 vol. 4, pp. 279-284.

* cited by examiner 1    2    3    4    5

16.9kD
14.4kD
10.7kD

SEQUENCE LISTING

<160> NUMBER OF SEQ ID NOS: 4

<210> SEQ ID NO 1
<211> LENGTH: 136
<212> TYPE: PRT
<213> ORGANISM: Artificial Sequence
<220> FEATURE:
<223> OTHER INFORMATION: Description of the Artificial Sequence: the
      amino acid sequence of the synthetic RGD-Sak

<400> SEQUENCE: 1

Ser Ser Ser Phe Asp Lys Gly Lys Tyr Lys Lys Gly Asp Asp Ala Ser
1               5                   10                  15

Tyr Phe Glu Pro Thr Gly Pro Thr Leu Met Val Asn Val Thr Gly Val
            20                  25                  30

Asp Gly Lys Arg Asn Glu Leu Leu Ser Pro Arg Tyr Val Glu Phe Pro
        35                  40                  45

Ile Lys Pro Gly Thr Thr Leu Thr Lys Glu Lys Ile Glu Tyr Tyr Val
    50                  55                  60

Glu Trp Ala Leu Asp Ala Thr Ala Tyr Lys Glu Phe Arg Val Val Glu
65                  70                  75                  80

Leu Asp Pro Ser Ala Lys Ile Glu Val Thr Tyr Tyr Asp Lys Asn Lys
                85                  90                  95

Lys Lys Glu Glu Thr Lys Ser Phe Pro Ile Thr Glu Arg Gly Asp Val
            100                 105                 110

```
Val Pro Asp Leu Ser Glu His Ile Lys Asn Pro Gly Phe Asn Leu Ile
        115                 120                 125

Thr Lys Val Val Ile Glu Lys Lys
    130                 135

<210> SEQ ID NO 2
<211> LENGTH: 408
<212> TYPE: DNA
<213> ORGANISM: Artificial Sequence
<220> FEATURE:
<223> OTHER INFORMATION: Description of the Artificial Sequence: the
      nucleic acid sequence encoding the synthetic RGD-Sak

<400> SEQUENCE: 2
tcaagttcat tcgacaaagg aaaatataaa aaaggcgatg acgcgagtta ttttgaacca     60
acaggcccgt atttgatggt aaatgtgact ggagttgatg gtaaaggaaa tgaattgcta    120 tccctcatt atgtcgagtt tcctattaaa cctgggacta cacttacaaa agaaaaaatt    180
gaatactatg tcgaatgggc attagatgcg acagcatata agagtttag agtagttgaa    240 ttagatccaa gcgcaaagat cgaagtcact tattttgata agaataagaa aaagaagaa    300 acgaagtctt tccctataac agaacgtggt gatgttgtcc cagatttatc agagcatatt    360
aaaaaccctg gattcaactt aattacaaag gttgttatag aaaagaaa                 408

<210> SEQ ID NO 3
<211> LENGTH: 136
<212> TYPE: PRT
<213> ORGANISM: Artificial Sequence
<220> FEATURE:
<223> OTHER INFORMATION: Description of the Artificial Sequence: the
      amino sequence of the synthetic KGD-Sak

<400> SEQUENCE: 3

Ser Ser Ser Phe Asp Lys Gly Lys Tyr Lys Lys Gly Asp Asp Ala Ser
  1               5                  10                  15

Tyr Phe Glu Pro Thr Gly Pro Thr Leu Met Val Asn Val Thr Gly Val
             20                  25                  30

Asp Gly Lys Arg Asn Glu Leu Leu Ser Pro Arg Tyr Val Glu Phe Pro
         35                  40                  45

Ile Lys Pro Gly Thr Thr Leu Thr Lys Glu Lys Ile Glu Tyr Tyr Val
     50                  55                  60

Glu Trp Ala Leu Asp Ala Thr Ala Tyr Lys Glu Phe Arg Val Val Glu
 65                  70                  75                  80

Leu Asp Pro Ser Ala Lys Ile Glu Val Thr Tyr Tyr Asp Lys Asn Lys
                 85                  90                  95

Lys Lys Glu Glu Thr Lys Ser Phe Pro Ile Thr Glu Lys Gly Asp Val
            100                 105                 110

Val Pro Asp Leu Ser Glu His Ile Lys Asn Pro Gly Phe Asn Leu Ile
        115                 120                 125

Thr Lys Val Val Ile Glu Lys Lys
    130                 135

<210> SEQ ID NO 4
<211> LENGTH: 408
<212> TYPE: DNA
<213> ORGANISM: Artificial Sequence
<220> FEATURE:
<223> OTHER INFORMATION: Description of the Artificial Sequence: the
      nucleic acid sequence encoding the synthetic KGD-Sak
```

-continued

```
<400> SEQUENCE: 4
tcaagttcat tcgacaaagg aaaatataaa aaaggcgatg acgcgagtta ttttgaacca      60
acaggcccgt atttgatggt aaatgtgact ggagttgatg gtaaaggaaa tgaattgcta     120 tccctcatt  atgtcgagtt tcctattaaa cctgggacta cacttacaaa agaaaaaatt    180
gaatactatg tcgaatgggc attagatgcg acagcatata aagagtttag agtagttgaa    240
ttagatccaa gcgcaaagat cgaagtcact tattttgata agaataagaa aaaagaagaa    300
acgaagtctt tccctataac agaaaaaggt gatgttgtcc cagatttatc agagcatatt    360
aaaaaccctg gattcaactt aattacaaag gttgttatag aaaagaaa                 408
```

RECOMBINANT STAPHYLOKINASE DERIVATIVES AND THE PREPARATION AND APPLICATIONS THEREOF

CROSS-REFERENCE TO RELATED APPLICATION(S)

This patent application is the national stage of an international application and claims priority to Chinese patent application, serial number CN00111627.4, filed on Jan. 28, 2000, the subject matter of which is incorporated by reference.

FIELD OF THE INVENTION

The present invention relates to novel recombinant staphylokinase derivatives. More particularly, the invention relates to the recombinant staphylokinase derivatives with a significant decrease in polymerizing ability as compared with wild-type staphylokinase and the bifunctionality of thrombolytics and anticoagulant. The invention also relates to the preparation of these staphylokinase derivatives, and to the application of these recombinant staphylokinase derivatives as a thrombolytic drug.

BACKGROUND OF THE INVENTION

The naturally occurring staphylokinase (Sak) is a proteolytic enzyme produced by the lysogenic phage: of *Staphylococcus aureus*, and consists of 136 amino acid residues. Indeed, Sak is not an enzyme in nature, but it forms a 1:1 complex with plasminogen (plg); in human plasma, which complex is then activated into Sak plm by the trace of plasmin (plm) on the surfaces of blood clots. Sak plm is a potent plasminogen activator to activate the free form of plg into plm, which in turn catalyzes the degradation of fibrin, the main matrix of thrombus, thus resulting in the lysis of thrombus. Sak has fibrin specificity in plg activation and acts more efficiently than other thrombolytic agents to lyse old thrombus and platelet-rich thrombus. Thus, Sak is an efficient and specific thrombolytic agent (Collen D et al, *Nature Medicine* 4, 279-284 (1998)). At present, recombinant staphylokinases are produced by several companies in the world, but they differ from each other in gene structures. The thrombolytic therapy of acute myocardial infarction (AMI) with recombinant staphylokinases studied by D. Collen of Belgium completed the clinical trial stage II. ShiXin Centre (Chengdu, China) also finished clinical trial stage I of AMI and the effect was quite good. In 1994 Shanghai Medical University constructed a Sak gene, accomplished the high level expression in *E. coli*, ad finished the pilot process. They have applied for the permission of clinical trials to treat acute cerebral infarction. However, as a heterologous protein, Sak may have strong antigenicity when administered to patients. Though no severe allergic reaction was reported in the clinical trials, Sak induced a high titer of neutralizing antibodies in most patients two weeks after administration, arguing against its repeated administration (Declerck P J et al, *Thromb Haemost* 71, 129-133 (1994)). Moreover, it was discovered in the study of recombinant staphylokinases that staphylokinases tend to form dimers, even polymers. The formation of polymers increases its immunogenicity.

During the thrombolytic therapy, thrombolytic drugs, are often combined with anti-thrombin or anti-platelet drugs such as heparin and aspirin to promote thrombolysis and to prevent reinfarction. Recent studies of thrombolytic auxiliary drugs are remarkable. Arg-Gly-Asp (RGD) and Lys-Gly-Asp (KGD) are functional sequences against platelet aggregation. They competitively bind to the glycoprotein membrane receptor IIb/IIIa associated with the platelet membrane aggregation, thus preventing the binding of fibrinogen to its receptor and blocking the reformation of thrombus (Frishman W H et al, *Am. Heart J.* 130, 877-892(1995); Nichols A J et al, *Trends Pharmacol. Sci* 13, 413-417(1992)). Introducing the RGD/KGD sequence into the cDNA of a thrombolytic agent e.g. urokinase under an appropriate conformational restriction, the product expressed will have the bifunctionality of thromboytics and anticoagulant (Smith J et al, *J. Biol. Chem.* 270, 30486-30490 (1995)). However, it was indicated in the clinical trials that the thrombolytic effect of urokinase was significantly lower than staphylokinase (50% versus 75%). Furthermore, various chemical mimics have been developed based on the RGD/KGD sequence such as Tirofiban, Lamifiban, Lefradafiban, Orbofiban, Xemilofiban, Integrinlin and the like, which could block the IIb/IIIa receptor. When administered in combination with thrombolytics, the incidence of reinfarction would be significantly decreased (Frishman W H et al, *Am. Heart J.* 130, 877-892 (1995); Verstraete M et al, 49, 856-884 (1995)).

The object of the invention is to provide novel staphylokinase derivatives, which escape from forming dimer and have the bifunctionality of thrombolytics and anticoagulant, and the preparation thereof.

BRIEF DESCRIPTION OF THE INVENTION

The present invention relates to novel staphylokinase derivatives, which escape from forming dimer and have the bifunctionality of thrombolytics and anticoagulant, and to the preparation and application thereof. In the present invention, novel Sak molecular structures were designed with structural biology and prepared by genetic engineering. Besides the efficient and specific thrombolytic effect, the resulting product have new properties such as low polymerizing ability and anti-platelet aggregation. The preparing process is simple and safe. The yield, Purity and activity of the products are substantially the same as that of wild-type Sak.

DETAILED DESCRIPTION OF THE INVENTION

Figure 1:
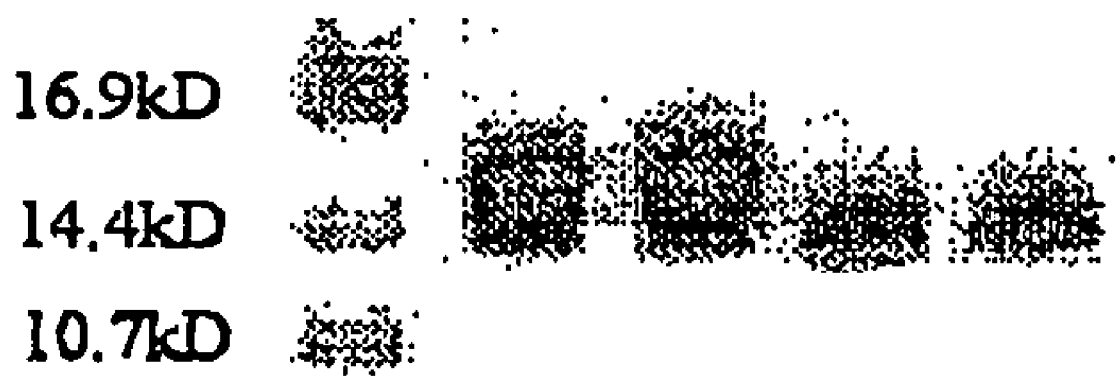
FIG. 1 shows the SDS-PAGE photograph of various concentrations of the wild-type and the recombinant staphylokinase of the present invention, wherein: lane 1, molecular standard lane 2, RGD-Sak (3 mg/ml); lane 3, RGD-Sak (30 mg/mL) lane 4, Sak (3 mg/ml) and lane 5, Sak (30 mg/ml).

Wild-type Sak is an ellipsoid molecule, which comprises an α-helix consisting of 12 amino acid residues covered by two β-sheets consisting of 5 and 2 β-strands respectively, extending from the amino acid residue 20. The 20 $NH_2$-terminal amino acids are extending outwards flexibly, whose functions can hardy be deduced from the crystal structure. Sak shows obvious asymmetry in hydropathy and the active region is largely at the hydrophile side (Zhan C H et al, *Acta Cryst.* D52, 564-565 (1996), Rabijns A et al, *Nat. Struct. Biol.* 5, (1997)). To determine the binding regions of the Sak dimer, molecular joining was performed with GRAMM V1.03 software developed by Vakser I A (Rockefeller University, USA) on the basis of the X-ray diffraction crystal structure of monomeric Sak. Using one Sak molecule as the receptor and another Sak molecule as the ligand, the Sak receptor was searched for the binding region with respect to the Sak ligand. 10 complex structures obtained by joining with the global high resolution joining parameters recommended by the author were searched. The modelling was performed on a SGI 02 graphic workstation.

TABLE 1

| Global high resolution joining parameters | |
|---|---|
| Matching mode (generic/helix) | mmode = generic |
| Grid step | eta = 1.7 |
| Repulsion (attraction is always −1) | ro = 30 |
| Attraction double range (fraction of single range) | fr = 0 |
| Potential range type (atom radius, grid step) | crang = atom radius |
| Projection (blackwhite, gray) | ccti = gray |
| Represention (all, hydrophobic) | crep = all |
| Number of matches to output | maxm = 10 |
| Angle for rotations, deg (10, 12, 15, 18, 20, 30, 0-no rot) | ai = 10 |

The electrostatic potential and hydrophobicity, analysis indicated that monomeric Sak was significantly asymmetric in hydropathy. Silence et al showed by random mutagenesis that amino acids determining the activity mainly situated on the hydrophilic side (Silence K et al, *J. Biol. Chem.* 270, 27192-27198 (1995)). The hydrophobic side of Sak has two main hydrophobic regions (HR), which lie at residues 47-56 (HR1) and 104-113(HR2) respectively, wherein HR2 is more hydrophobic. In the structure mode of the dimer constructed, the interaction between the hydrophobic regions is very important and has two binding manners, HR1-HR2 and HR2-HR2. Because HR1 is close to the active region, the active region of one Sak molecule will be covered when two Sak molecules bind to each other in the manner of HR1-HR2, probably retaining the activity of one Sak molecule only. When they bind to each over in the manner of HR2-HR2, the activity appears not to be influenced largely.

The interface of protein interface on is usually between 600 and 1300 Å$^2$, and each molecule provides 10-30 contacting residues. However, there is a so-called "hot spot" in the interface in which only 3-5 amino acids provide about 80% of the binding energy. The change of these residues will result in significant decrease of the binding ability of the complex (Li B et al, *Science* 270, 1657-1660 (1995)). Thus, irrespective of the particular binding manner of the dimer, the formation of dimers will probably be prevented when the main binding residues of the HR2 are changed. Phe111, to strongly hydrophobic amino acid, situates in the core region of, HR2 and is far away from active region. In a preferred embodiment of the invention, it is replaced by Asp, a strongly polar amino acid, to disrupt the hydrophobic effect. The mutant was expected to retain the activity. Further, since peptides of RGD/KGD sequence can inhibit platelet aggregation, and the loop region within the β-sheets is quite free in conformation, Lys109 was changed into Arg in the present invention, resulting in a RGD-Sak sequence, or Lys109 was not changed, which results in a KGD/Sak sequence. The amino acid sequence of RGD-Sak of the invention is set forth it SEQ ID NO: 1, and the amino acid sequence of KGD-Sak is set forth in SEQ ID NO: 3.

In another aspect, the present invention relates to a method for the production of the staphylokinase derivatives of the present invention, which comprises: preparing a DNA fragment comprising at least the part of the coding sequence of staphylokinase that provides for its biological activity; performing in vitro site-directed mutagenesis on the DNA fragment to replace one or more codons for wild-type amino acids with a codon or codons for another (other) amino acid(s); cloning the mutated DNA fragment into a suitable vector; transforming or transfecting a suitable host cell with the recombinant vector; culturing the host cell under conditions suitable for the expression of the DNA fragment; and recovering and purifying the desired staphylokinase derivatives from the culture medium.

The site-directed mutagenesis can be performed by polymerase chain reaction (PCR). In a preferred embodiment a first amplification is carried out by using a backward-primer and mutating-primer, with plasmid pST-Sak as the template. After recovered and purified by agarose gel electrophoresis, the double stranded fragment amplified was used as a primer to carry out a second amplification with a forward-primer using plasmid pST-Sak as template again. Following purifications the fragment obtained is used as a template in a third amplification together with the forward-primer and the backward-primer. The product was blunted with Klenow fragment, EcoRI and BamHI digested, ligated with EcoRI/BamHI digested pUC19, and transformed into *E. coli* strain JM109. A positive clone was selected by screening through digestion analysis, and the presence of the desired mutation at the expected position was verified by nucleotide sequence analysis. The sequencing analysis was performed by Genecore Biotechnology Co on an ABI 377 sequencer. Then, the RGD-Sak gene was removed by EcoRI and BamHI digestion, and ligated into the corresponding site of expression vector pLY4.

```
SEQID:5 forward-primer:
5'-CGC GAA TTC ATG TCA AGT TCA TTC GAC-3'

SEQID:6 backward-primer:
5'-CGC GGA TCC TTA TTT CTT TTC-3'

SEQID:7 mutating-primer(I):
5'-TAA ATC TGG GAC GAC GTC ACC ACG TTC TGT TAT
AGG-3'(a PstI site introduced, used to construct a
RGD-Sak gene)

SEQID:8 mutating-primer(II):
5'-ATC TGG GAC GAC GTC ACC TTT TTC TG-3'
(a PstI site introduced, used to construct a KGD-
Sak gene)
```

Different DNA fragments comprising the nucleotide sequences coding for the staphylokinase derivatives of the present invention can be prepared following the above method. These fragments comprise the nucleotide sequence set forth in SEQ ID NO: 2 or SEQ ID NO: 4.

Recombinant expression plasmids were obtained by ligating the DNA fragments of the invention to an expression vector. The invention is not limited to any particular expression vector provided that it can be recombined with the above DNA fragment yielding plasmids suitable for expression. In a preferred embodiment of the invention, a prokaryotic expression vector is used for example pLY-4, T7 expression system, PL expression system and the like.

The above recombinant expression vector may be introduced into a suitable host cell by conventional procedures. The invention is not limited to any particular host cells, provided that they can express the recombinant expression vectors. In a preferred embodiment of the invention, an *E. coli* strain, is used, for example K802, JF1125, JM series, DH5α, and the likes.

The expression product of the invention was present as inclusion bodies in the engineered cells. The desired product can be isolated and purified from the inclusion bodies by conventional procedures, for example disrupting the cells by a French press and collecting the inclusion bodies by centrifugation.

For all basic manipulations of the molecular biology in above embodiments, see *Molecular Cloning, A laboratory Manual*.

Furthermore, the nucleic acids and the corresponding polypeptides of the invention include the sequences that are different from the sequences set forth in SEQ ID NO: 1-4 due to silent mutations. These sequence modifications include for example nucleotide substitutions that do not alter the amino acid sequence (for example, different codons for the same amino acid or degenerate sequences). The amino acid sequences of the homologous polypeptides may differ from that of SEQ ID NO: 1 or SEQ ID NO: 3 in that one or more amino acid residues are inserted deleted or replaced with other different amino acid residues. Preferably, the amino acid changes are of minor nature, i.e. conservative amino acid substitutions which will not influence the folding and/or activity of the protein significantly; small deletions, usually of 1 to about 30 amino acids in length, small extensions at amino or carboxyl terminus, e.g. the methionine residue at amino terminal; small connective peptide up to about 20-25 residues in length; or small extensions that will facilitate purification by changing the net charge or that have other functions, e.g. poly-histidine tract, antigenic epitopes or binding domains.

The present inventor discovered that the thrombolytic and anticoagulant functions of the expression products remained almost unchanged when the coding sequence of the 6-10 amino acids $NH_2$-terminal of RGD-Sak or KGD-Sak was removed by deletion mutation; the thrombolytic activity of the expressions was lost when the coding sequence of the 10-15 $NH_2$-terminal amino acids was removed; and the above bifunctionality of the expression products remained almost unchanged when the coding, sequence of the 15 $NH_2$-terminal amino acids was removed and the Ser at position 16 was changed to Lys.

EXAMPLE 1

Design, Preparation and Characterization of RGD-Sak a. The Identification of Wild-Type r-Sak Wild-type r-Sak, prepared by our laboratory (970923) was more than 98% pure and stored at −70° C.

Reductive and non-reductive SDS-PAGE performed according to the method of Laemmli (see *Molecular Cloning, A Laboratory Manual*).

Loading buffer: containing 0.0625 mol/L Tris-HCl pH6.7, 2% SDS, 10% glycerol, 5% mercaptoethanol and 0.001% bromophenol blue.

Sample treating and loading a vial of lyophilized sample (3 mg/vial, stored at −70° C. for more tan 3 months) was dissolved in 3 ml dd$H_2O$. The loading volume was 10 μl.

Gel staining: Coomassie brilliant blue R-250 or silver staining

Scanning the protein bands in the gel: scanning with ImageMaster® VDS (Pharmacia) and analyzing the amount of protein contained in each bands with appended software.

After electrophoresis, the gel is stained with Coormassie brilliant blue, and dense bands appeared at positions corresponding to relative molecular weights of about 15.5 kD, 31 kD, 46 kD and 62 kD.

Determining the activities by inverted casein gel plate method the above gel was sequentially washed with 2.5% Triton X-100 solution and distilled water thoroughly, placed on the agar gel plate (comprising 1% agar) containing fibrinogen, human plasminogen and thrombin, and incubated at 37° C. for 8 hours. Clear lysis bands appeared at positions corresponding to the above molecular weights, suggesting that wild-type r-Sak tends to form anti-SDS polymers during the storage of wild-type r-Sak, which is stable and active.

b. The Molecular Simulation of the Staphylokinase Dimer and Reasonable Design of Mutants The modeling work was performed on a SGI 02 graphic workstation with GRAMM V1.03, a molecule joining software developed by I. A. Vakser (Rockefeller University, USA).

To determine the binding region of Sak dimer, Sak-to-Sak joining was made with GRAMM V1.03 on the basis of the X-ray diffraction crystal structure of monomeric Sak.

Phe111 was replaced with Asp, a strongly polar amino acid in the invention to disrupt the hydrophobic interaction. The mutant was expected to retain the activity. Further, since peptides of RGD sequence can inhibit platelet aggregation and the loop region)), within the β-sheets is quite free in conformation Lys109 was also changed to Arg to yield RGD sequence.

c. The Cloning of RGD-Sak Gene and the Construction of Prokaryotic Expression Plasmid Using pST-Sak as template, a first amplification was carried out with the forward-primer and mutating-primer (II) shown below. After the 351 bp fragment amplified was recovered from agarose gel and purified, it was used to carry out a second amplification with the backward-primer shown below, using pST-Sak as template again. Following purification, using the 408 bp fragment as template a third amplification was carried out with the forward-primer and the backward-primer. The product was blunted with Klenow fragment EcoRI and BamHI digested, ligated to pUC19, and transformed. A positive clone was selected by digestion analysis, and the presence of the desired mutations was verified by nucleotide sequence analysis. The sequence analysis was performed by Genecore Biotechnology Co. on an ABI 377 sequencer. Then, the KGD-Sak gene was removed by EcoRI and BamHI digestion, and ligated into the corresponding site of the expression vector pLY-4.

```
SEQID:5 forward-primer:
5'-CGC GAA TTC ATG TCA AGT TCA TTC GAC-3'

SEQID:6 backward-primer:
5'-CGC GGA TCC TTA TTT CTT TTC-3'

SEQID:8 mutating-primer(I):
5'-ATC TGG GAC GAC GTC ACC TTT TTC TC-
3'(a PstI site introduced)
```

All nucleic acid modifying enzymes were purchased from GIBCO BRL and Promega. Oligonucleotides were synthesized by DNA Synthesis Group of Johns Hopkins University (USA).

*E. coli* strain JM109 and pUC19 were kept by our laboratory *E. coli* strain JF1125 and prokaryotic expression vector pLY-4 were kindly provided by Prof. Xin-Huan Liu of the Institute of Biochemistry of the Chinese Academe of Science (China). pST-Sak was constructed by our laboratory (Chinese Patent NO. 94 1 12105.4).

The gene of interest was ligated into pLY-4 aid transformed into *E. coli* strain JF1125. The plasmid was prepared and identified by corresponding digestion analysis. The characteristic fragment was obtained, verifying the positive clone.

The *E. coli* strain JF1125 transformed with pLY-4 RGD-Sak was cultured in M9CA culture medium at 30° C. until OD600 reached 0.6. Then the temperature was increased to 42° C. and the culturing was continued for another 3 hours to induce expression. The product expressed was analyzed by SDS-PAGE. After the electrophoresis, one half was stained by Coomassie brilliant blue. A dense band was observed at a molecular weight of about 15.5 kD in the lane of the lysate of induced bacterial cells, which accounted for more than 50% of the total proteins of the bacterial cells as judged by scanning. The other half was placed on a casein gel plate after SDS was removed, and incubated at 37° C. for several hours. There was a clear region corresponding to 15.5 kD. In other words, casein at this position was degraded, suggesting that RGD-Sak had a fibrolytic activity. After the cells were crushed and centrifuged, it was discovered that the 15.5 kD band was mainly present in the pellet, while it could hardly be observed in the supernatant indicating that the product expressed exists as inclusion bodies d. Inducible Expression in Engineered Strains The engineered strains were screened for high lever of expression (e.g. the recombinant protein expressed accounted for more than 50% of the total protein of the cell). Low density fermentation was carried out with the strain selected in a 10 L fermentor. After 3 hours of temperature induction culturing, cells were spun down, washed in PBS, and stored at −70° C. until use 80 g wet cells were obtained from a 10 L culture. The wet cells were suspended in PB buffer, disrupted by a high pressure homogenizer and centrifuged. Samples were taken for SDS-PAGE. The results indicated that the protein of interest was present in the lane of the pellet with a band stained densely at the position of a molecular weight of 15.5 kD, and that hardly any stain could be observed at the corresponding position of the supernatant, suggesting that RGD-Sak mainly exists as inclusion bodies.

e. Isolation, Solubilization and Renaturation of Inclusion Bodies

After disrupting by pressing, 80 g cells of the engineered strain were centrifuged at 10,000 rpm and 20 g inclusion bodies was obtained. After the inclusion bodies was washed in 0.05 mol/L PB and centrifuged at 5,000 rpm, it was dissolved in a solution containing 0.1 mol/L PB pH5.0, 6 mol/L, guanidium hydrochloride, 0.5% β-mercaptoethanol, and incubated at room-temperature until the solution became clear. After ultracentrifugation at 30,000 rpm the pellet was discarded and the supernatant was diluted for renaturation in 0.1 mol/L PB pH5.0 and 0.5% β-mercaptoethanol f. Sephadex G-10 and S-Sepharose FF Column Chromatography After concentration by ultrafiltration (MW 1000, Millipore) the supernatant was filtrated through a Sephadex G-10 column. The filtrate was applied to an S-Sepharose FF column equilibrated previously by 10 bed volumes of 0.1 mol/L PB buffer pH 5.0. A chromatograph (Waters) was used to control the flow rate and to detect the protein peak. After loading, the column was washed to baseline with PB buffer and eluted with a 0-1 mol/L gradient of NaCl. The fractions eluted were collected. The distribution of the desired protein was analyzed by SDS-PAGE and the concentration determined by Bradford method (the reagents used were purchased from Bio-Rad).

All chromatography operations were of routine work to those skilled in the art.

g. The Identification of the Purity and the Determination of the Molecular Weight.

The sample was analyzed by SDS-PAGE according to *Molecular Cloning, A Laboratory Manual*. After stained with Coomassie brilliant blue R-250, the gel was scanned with Pharmacia Imagemaster VDS to determine the purity and molecular weight of the protein. Consequently, it was determined that the purity was above 95% and that the molecular weight was about 15.5 kD h. The Determination of the Biological Activity Casein gel plaque method (Pipemo A G et al, *J. Exp. Med.* 48(1), 223-234 (1978)) and chromogenic substrate method (Lijnen H R et al, *J. Biol. Chem.* 266, 11826-11832 (1991)) were carried out to determine the biological activity. The specific activity was about 90,000-100,000 HU/mg. For the definition of the Unit, see Tang Q-Q et al, *Drug Biotechnology (Chinese)* 4(1), 1-4(1997).

i. The Determination of the Km and Kcat Value of Sak Plasmin Complex and RGD-Sak Plasmin Complex 2 μmol/L Sak or RGD-Sak was incubated with 2 μmol/L plasminogen respectively in 0.1 mol/L PB pH5.0 at pH7.4 and 37° C. for 30 min to form complexes with plasmin. Then catalytic amount of complex was taken (5 nM) to react for 0-10 min in the following systems in 0.1 M PB at pH7.4 and 37° C., and OD405 was recorded every 30 sec. Each concentration of plasminogen was assayed in triplicates and averaged.

| Reaction System | Final Concentration |
|---|---|
| Sak · plasmin (RGD-Sak · plasmin) | 5 nmol/L |
| chromogenic substrate | 1 mol/L |
| plasminogen | 1-30 μmol/L |

The activation of plasminogen by RGD-Sak plasmin corresponded to the Michaelis-Menten equation (table 1)

TABLE 1 the comparison of enzymatic kinetic constants of the plasminogen activation by RGD-Sak · plasmin and Sak · plasmin

| | Km(μmol · L$^{-1}$) | Kcat(s$^{-1}$) | Kcat/Km |
|---|---|---|---|
| Sak · plasmin | 6.42 | 1.03 | 0.16 |
| RGD-Sak · plasmin | 12.50 | 1.41 | 0.11 | j. The Test of Polymerizing Ability

Wild-type Sak was used as a control. The samples were dissolved in physiological saline. Two protein concentrations, 30 mg/ml (high) and 3 mg/ml (low), were tested. The solutions were kept at room temperature. Samples were taken every 24 hr and analyzed by electrophoresis.

At both protein concentrations, the polymerizing ability of RGD-Sak was significantly lower than that of wild-type Sak (FIG. 1).

k. The Sensitizing Test on Guinea Pigs

Both recombinant wild-type Sak and mutant RGD-Sak were dissolved in sterile physiological saline at a concentration of 2500 U/ml for the sensitizing test. For each administration intact vials were taken to prepare the fresh solutions in a sterile way, 20 healthy guinea pigs were assigned to two groups randomly, with 10 guinea pigs each. The guinea pigs were i.p. injected with r-Sak or RGD-Sak at a dose of 0.15 mg/kg every other day for three times. A first and a second i.v.

attack at 0.3 mg/kg were performed on day 14 and 21, respectively. 2 healthy and non-injected: guinea pigs were: i.v. injected with above samples at 0.3 mg/kg and observed for other presence of similar response to exclude the pharmacological and pathological interference of the samples.

The group injected with wild-type r-Sak 8 guinea pigs showed a positive response of grade IV and 2 showed, a positive response of grade II.

The group injected with RGD-Sak: 2 guinea pigs showed a positive response of grade I and the others showed no obvious response.

| Grade I response: | mild cough |
|---|---|
| Grade II response: | cough several times, quiver |
| Grade III response: | quiver violently |
| Grade IV response: | convulsion, spasm, incontinence of the feces and urine, shock to death |

Figure 2:
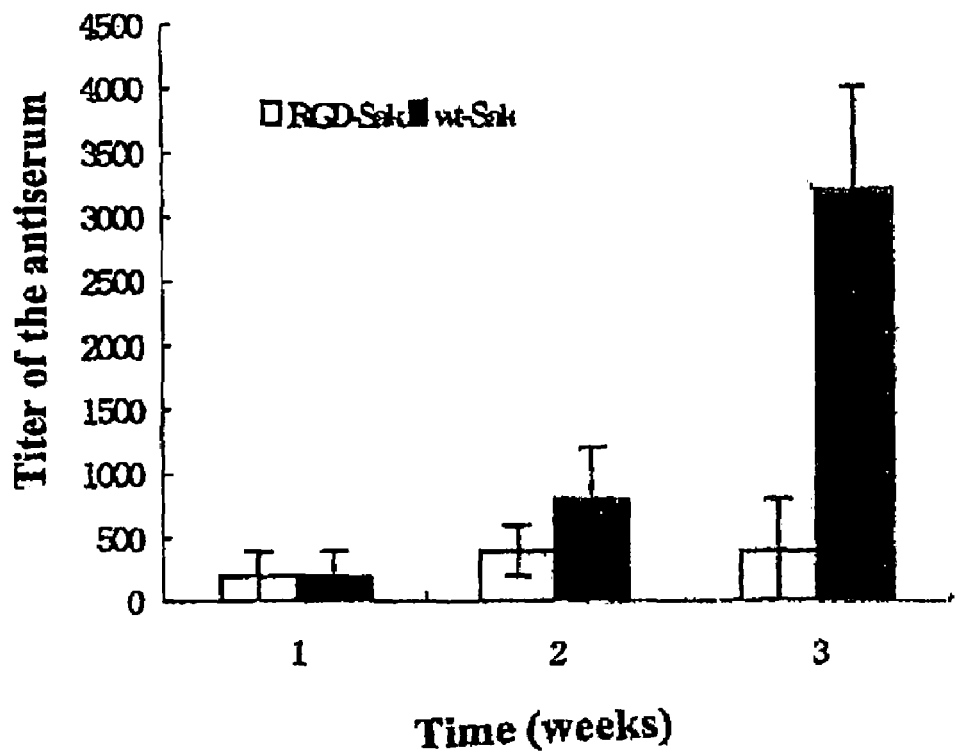
FIG. 2 shows the results of sensitizing test of wild-type staphylokinase and RGD-Sak on guinea pigs.

The antibody levels in the sera from the guinea pigs, immunized for 1-3 weeks were tested by ELISA, wherein wt-Sak and RGD-Sak were used as antigens, respectively. In the fist week, the antibodies against either antigen were low. In the second week, the antibody level of the wt-Sak group (n=10) increased to 1:800, whereas the antibody lever of the RGD-Sak group (n10) was 1:400. In the third week, the wt-Sak group increased to 1:3200, whereas the RGD-Sak group remained at 1:400. Thus, the immunogenicity of the RGD-Sak decreased significantly as compared with wt-Sak (FIG. 2B).

The above results indicated that the immunogenicity of the RGD-Sak was decreased significantly as compared with wt-Sak.

l. The Platelet Aggregation Inhibitory Assay

Fresh blood anticoagulated with 1/10 volume of 110 mmol/L sodium citrate was centrifuged slowly (150 g, 10 min) to get the platelet-rich plasma (HRP). RGD-Sak was added to HRP to a final concentration of 2 $\mu$mol/L and the mixture was incubated at 37° C. for 2 min with continuous stirring. Then ADP was added to a final concentration of 2 $\mu$mol/L as an inducer. The platelet aggregation rate was determined within 5 min with a two-channel platelet aggregator (CHRONO-LOG560). Wild-type r-Sak. (2 $\mu$mol/L) and physiological saline were assayed as controls. ADP was purchased from Sigma and other reagents were of analytic grade made in China.

Figure 3:
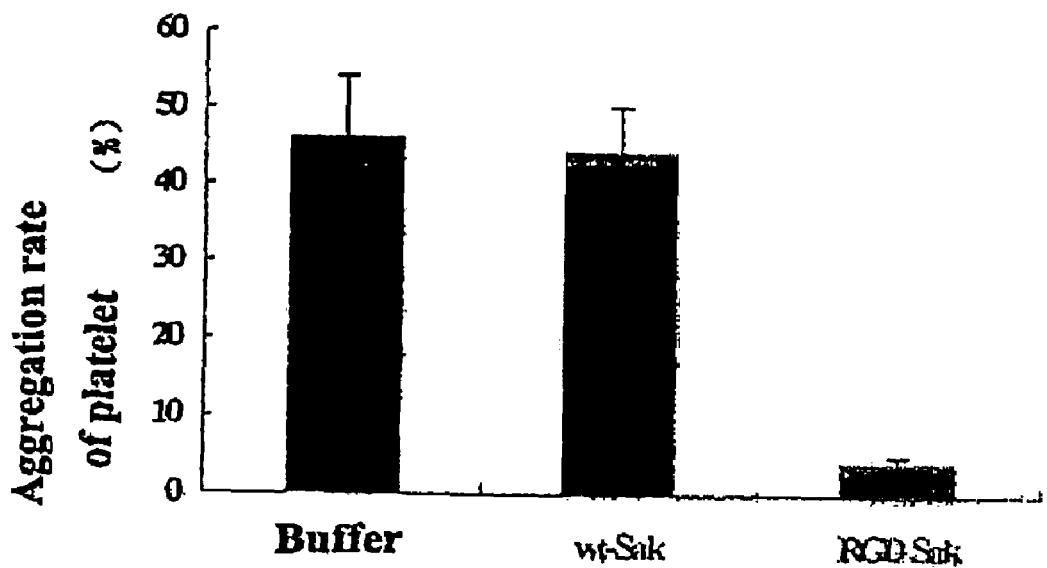
FIG. 3 shows the results of anti-platelet-aggregation test of RGD-Sak.

Consequently, the aggregation rate of the RGD-Sak, group (5%±2%, n=3) was significantly lower than that of the RGD-Sak group (58%±3%, n=3) and that of the physiological saline group (59%±3%, n=3), suggesting that RGD-Sak has a powerful potency to inhibit platelet aggregation induced by ADP (FIG. 3).

m. The Thrombolytic Assay on Animals

The animal thrombolytic assay was performed with RGD-Sak prepared in the present invention, verifying that RGD-Sak retained the same thrombolytic property as that of wild-type Sak.

(i) Treating experimental rabbit femoral artery thrombosis with RGD-Sak: the treatment group of RGD-Sak, the treatment group of wild-type Sak and the control group of blank each consisted of 6 animals. It was indicated by arteriography that the femoral artery under the middle segment was not visible before treatment. When photography was repeated 60 minutes after i.v. injection of 0.1 mg/kg RGD-Sak, the femoral artery was filled thoroughly and the blood cycle was recovered which was consistent with the wild-type Sak group, while in the control group, the femoral artery did not appear to be filled.

(ii) Treating experimental rabbit hyphema with RGD-Sak the treatment group of RGD-Sak, the treatment group of wild-type Sak and the control group of blank each consisted of 6 animals, 4 hours after intraocular injection of 10-20 $\mu$g RGD-Sak, it was observed that the hyphema clot was lysed and the red blood cells settled and formed an interface with aqueous humor. The intraocular hematocele was eliminated after 24 hours. This is consistent with the wild-type Sak group. However, the hyphema in the control group was not significantly changed.

(iii) RGD-Sak thrombolytic therapy was safe and efficient for induced by the treatment of acute myocardial infarction experimental dog coronary arterial thrombosis. The experimental group consisting of 6 animals was given RGD-Sak at 0.3 mg/kg body weight by i.v. infusion; and the control group consisting of 6 animals was given physiological saline instead of RGD-Sak by i.v. infusion Coronary arteriography was carried out before and after dosing. Before administration, it was shown that the left anterior descending branch of the coronary artery was unfilled or filled incompletely in the animals of both groups. Arteriography was performed 30 minutes after treatment. It was shown that the left anterior descending branch was refilled in the animals of the experimental group, and the animals survived. As for the control group, there was no significant change in the region filled incompletely and the animals died several hours later.

(iv) RGD-Sak thrombolytic therapy was safe and efficient the treatment of acute cerebral infarction induced by experimental pig intracranial arterbial thrombosis. The experimental group-consisting of 6 pigs was given RGD-Sak at 0.2 mg/kg body weight by i.v. infusion; and the control group consisting of 6 pigs was given physiological saline instead of RGD-Sak by i.v. infusion. Intracranial DSA arteriography was performed before and after administration. Before administration, it was shown that there were some intracranial arteries filled incompletely in the animals of both groups. Angiography was performed 30 minutes after treatment. It was shown that the intracranial arteries were refilled in the animals of the experimental group, and the animals survived. As for the control group, there was no significant change in the intracranial arteries filled incompletely and the animals died several days later.

EXAMPLE 2

Design, Preparation and Characterization of KGD-Sak a. Identification of Wild-Type r-Sak Wild-type r-Sak, prepared by our laboratory (970923), was more than 98% pure and stored at −70° C.

Reductive and non-reductive SDS-PAGE; performed according to the method of Laemmli (see *Molecular Cloning, A Laboratory Manual*).

Loading buffer: containing 0.0625 mol/L, Tris-HCl pH6.7, 2% SDS, 10% glycerol, 5% mercaptoethanol and 0.001% bromophenol blue.

Sample treating and loading: a vial of lyophilized sample (3 mg/vial, stored at −70° C. for more than 3 months) was dissolved in 3 ml ddH$_2$O. The loading volume was 10 $\mu$l.

Gel staining: Coomassie brilliant blue R-250 or silver straining.

Scanning the protein bands in the gel, scanning with ImageMaster® VDS (Pharmacia) and analyze the amount of protein contained in each bands with appended software.

After electrophoresis, the gel is stained with Coomassie brilliant blue, and dense bands appeared at positions corresponding to relative molecular weights of about 15.5 kD, 31 kD, 46 kD and 62 kD.

Determining the activities by inverted casein gel plate method the above gel was sequentially washed with 2.5% Triton X-100 solution and distilled water thoroughly, placed on the agar gel plate (comprising 1% agar) containing fibrinogen, human plasminogen and thrombin, and incubated at 37° C. for 8 hours. Clear lysis bands appeared at positions corresponding to the above molecular weights suggesting that wild-type r-Sak tends to form anti-SDS polymers during the storage of wild-type r-Sak, which is stable and active b. Molecular Simulation of the Staphylokinase Dimer and Reasonable Designing of Mutants The modeling work was performed on a SGI 02 graphic workstation with GRAMM V1.03, a molecule joining software developed by I. A. Vakser (Rockefeller University, USA).

To determine the binding region of dimeric Sak, Sak-to-Sak joining was made with GRAMM V1.03 on the basis of the X-ray diffraction crystal structure of monomeric Sak.

Phe111 was replaced with Asp, a strongly polar amino acid, in the invention to disrupt the hydrophobic interactions. The mutant was expected to retain the activity. Further, singe peptides of KGD sequence can inhibit platelet aggregation and the loop region within the β-sheets is quite free in conformation, the thrombolytic activity was not expected to be affected.

c. Cloning of KGD-Sak Gene and the Construction of Prokaryotic Expression Plasmids Using pST-Sak as template, a first amplification was carried out with the forward-primer and mutating-primer(I) shown below. After the 351bp fragment amplified was recovered from agarose gel and purified, it was used to carry out a second amplification with the backward-primer shown below, using pST-Sak as template again Following purification, using the 408bp fragment as template, a third amplification was carried out with the forward-primer and the backward-primer. The product was blunted with Kienow fragment, EcoRI and BamHI digested, ligated to pUC 19, and transformed. A positive clone was selected by digestion analysis, and the presence of the desired mutations was verified by nucleotide sequence analysis. The sequence analysis was performed by Genecore Biotechnology Co. on an ABI 377 sequencer. Then, the RGD-Sak gene was removed by EcoRI and BamHI digestion, and ligated into the corresponding site of the expression vector pLY-4.

```
SEQID:5 forward-primer:
5'-CGC GAA TTC ATG TCA AGT TCA TTC GAC-3'

SEQID:6 backward-primer:
5'-CGC GGA TCC TTA TTT CTT TTC-3'

SEQID:7 mutating-primer(I):
5'-TAA ATC TGG GAC GAC GTC ACC ACG TTC TGT TAT
AGG-3' (a PstI site introduced)
```

All nucleic acid modifying enzymes were purchased from GIBCO BRL and Promega Oligonucleotides were synthesized by DNA Synthesis Group of Johns Hopkins University (USA).

E. coli strain JM109 and pUC19 were kept by our laboratory. E. coli strain JF1125 and prokaryotic expression vector pLY-4 were kindly provided by Prof. Xin-Huan Liu of the institute of Biochemistry of the Chinese Academe of Science (China). pST-Sak was constructed by our laboratory (Chinese Patent).

The gene of interest was ligated into pLY-4 and transformed into E. coli strain JF1125. The plasmid was prepared and identified by corresponding digestion analysis. The characteristic fragment was obtained, verifying the positive clone.

The E. coli strain JF1125 transformed with PLY 4 KGD-Sak was cultured in M9CA culture medium at 30° C. until OD600reached 0.6. Then the temperature was increased to 42° C. and the culturing was continued for another 3 hours to induce expression. The product expressed was analyzed by SDS-PAGE. After the electrophoresis one half was strained by Coomassie brilliant blue. A dense band was observed at a molecular weight of about 15.5 kD in the lane of the lysate of induced bacterial cells, which accounted for more than 50% of the total proteins of the bacterial cells as judged by scanning. The other half was placed on a casein gel plate after SDS was removed, and incubated at 37° C. for several hours. There was a clear region corresponding to 15.5 kD. In other words, casein at this position was degraded, suggesting that KGD-Sak had fibrolytic activity. After the cells were crushed and centrifuged, it was discovered that the 15.5 kD band was mainly present in the pellet, while it could hardly be observed in the supernatant indicating that the product expressed exists as inclusion bodies.

d. The Inducible Expression in the Engineered Strain

The engineered strains were screened for high level of expression (e.g. the recombinant protein expressed accounted for more than 50% of the total protein of the cell). Low density fermentation was carried out with the strain selected in a 10 L fermentor. After 3 hours of temperature induction culturing, cells were spun down, washed in PBS, and stored at −70° C. until use. 80 g wet cells were obtained from a 10 L culture. The wet cells were suspended in PB buffer, disrupted by a high pressure homogenizer, and centrifuged. Samples were taken for SDS-PAGE. The result indicated that the protein of interest was present in the lane of the pellet with a band stained densely at the position of a molecular weight of 15.5 kD, and that hardly any stain could be observed at the corresponding position of the supernatant, suggesting, that RGD-Sak mainly exists as inclusion bodies.

e. Isolation, Solubilization and Renaturation of Inclusion Bodies

After disruption by pressing, 80 g cells of the engineered strain were centrifuged at 10,000 rpm and 20 g inclusion bodies was obtained. After the inclusion bodies was washed in 0.05 mol/L PB, pH5.2 and centrifuged at 5,000 rpm, it was dissolved in a solution containing 0.1 mol/L PB pH 5.2, 6 mol/L guanidium, hydrochloride, 0.5% β-mercaptoethanol, and incubated at room temperature until the solution became clear. After ultracentrifugation at 30,000 rpm, the pellet was discarded and the supernatant was diluted for renaturation in 0.1 mol/L PB pH5.0 and 0.5% β-mercaptoethanol.

f. Sephadex G-10 and S-Sepharose FF Column Chromatography

After concentration by ultrafiltration (MW 1000, Millipore), the supernatant was filtrated through a Sephadex G-10 column. The filtrate was applied to an S-Sepharose FF column equilibrated previously by 10 bed volumes of 0.1 mol/L PB buffer pH5.0. A chromatograph (Waters) was used to control the flow rate and to detect the protein peak. After loading, the column was washed to baseline with PB buffer and eluted with a 0-1 mol/L gradient of NaCl. The fractions eluted, were collected. The distribution of the desired protein was analyzed by SDS-PAGE and the concentration determined by Bradford method (the reagents used were purchased from Bio-Rad).

All chromatography operations were of routine work to those skilled in the art.

g. The Identification of the Purity and the Determination of the Molecular Weight The sample was analyzed by SDS-PAGE according to *Molecular Cloning, A Laboratory Manual*. After strained with Coomassie brilliant blue R-250, the gel was scanned with Pharmacia Imagemaster VDS to determine the purity and molecular weight of the protein. Consequently, it was determined that the purity was above 95% and that the molecular weight was about 15.5 kD.

h. The Determination of the Biological Activity

Casein gel plaque method (Pipemo A G et al, *J. Exp. Med.* 48(1) 223-234 (1978)) and chromogenic substrate method (Lijnen H R et al, *J. Biol. Chem.* 266, 11826-11832 (1991)) were carried out to determine the biological activity. The specific activity was about 90,000-100,000 HU/mg. For the definition of the unit, see Tang Q-Q et al, *Drug Biotechnology (Chinese)* 4(1), 1-4(1997).

i. Determination of the Km and Kcat Value of Sak Plasmin Complex and KGD-Sak Plasmin Complex 2 μmol/L Sak or RGD-Sak was incubated with 2 μmol/L plasminogen respectively in 0.1 mol/L PB at pH7.4 and 37° C. for 30 min to form complexes with plasmin. Then catalytic amount of complex was taken (5 nM) to react for 0-10 min in the following systems in 0.1M PB at pH7.4 and 37° C., and OD405 was recorded every 30 sec. Each concentration of plasminogen was assayed in triplicates and averaged.

| Reaction System | Final Concentration |
|---|---|
| Sak · plasmin (KGD-Sak · plasmin) | 5 nmol/L |
| chromogenic substrate S-2390 | 1 mmol/L |
| plasminogen | 1-30 μmol/L |

The activation of plasminogen by KGD-Sak plasmin corresponded to the Michaelis-Menten equation (table 2).

TABLE 2 the comparison of enzymatic kinetic constants of the plasminogen activation by KGD-Sak · plasmin and Sak · plasmin

|  | Km(μmol · L$^{-1}$) | Kcat(s$^{-1}$) | Kcat/Km |
|---|---|---|---|
| Sak · plasmin | 6.51 | 1.06 | 0.16 |
| RGD-Sak · plasmin | 14.10 | 1.46 | 0.10 | j. Test of Polymerizing Ability

Wild-type Sak was used as a control. The samples were dissolved in physiological saline. Two protein concentrations 30 mg/ml (high) and 3 mg/ml (low), were tested. The solutions were kept at room temperature. Samples were taken every 24 hr and analyzed by electrophoresis.

At both protein concentrations, the polymerizing ability of KGD-Sak was significantly lower than that of wild-type Sak.

k. The Sensitizing Test on Guinea Pigs

Both recombinant wild-type Sak and mutant KGD-Sak were dissolved in sterile physiological saline at a concentration of 2500 U/ml for the sensitizing test. For each administration, intact vials were taken to prepare the fresh solutions in a sterile way 20 healthy guinea pigs were assigned to two groups randomly, with 10 guinea pigs each. The guinea pigs were i.p. injected with r-Sak or KGD-Sak at a dose of 0.15 mg/kg every other day for three times. A first and a second i.v. attack at 0.3 mg/kg were performed on day 14 and 21, respectively. 2 healthy and non-injected guinea pigs were i.v. injected with above samples at 0.3 mg/kg and observed for the presence of similar response to exclude the pharmacological and pathological interference of the samples.

The group injected with wild-type r-Sak: 8 guinea pigs showed a positive response of grade IV and 2 showed a positive response of grade II.

The group injected with KGD-Sak: 1 guinea pig showed a positive response of grade I and the others showed no obvious response.

| | |
|---|---|
| Grade I response: | mild cough |
| Grade II response: | cough several times, quiver |
| Grade III response: | quiver violently |
| Grade IV response: | convulsion, spasm, incontinence of the feces and urine, shock to death |

The antibody levels in the sera from the guinea pigs immunized for 1-3 weeks were tested by ELISA, wherein wt-Sak and KGD-Sak were used as antigens, respectively. In the first week the antibodies against either antigen were low. In the second week, the antibody level of the wt-Sak group (n=10) increased to 1:800 whereas the antibody lever of the KGD-Sak group (n=10) was 1:200. In the third week, the wt-Sak group increased to 1:3200, whereas the RGD-Sak group increased to 1:400. Thus, the immunogenicity of the KGD-Sak decreased significantly as compared with wt-Sak.

The above results indicated that the immunogenicity of the KGD-Sak was decreased significantly as compared with wt-Sak.

l. The Platelet Aggregation Inhibitory Assay

Fresh blood anticoagulated with 1/10 volume of 110 mmol/L sodium citrate was centrifuged slowly (150 g, 10 min) to get the platelet-rich plasma (HRP). RGD-Sak was added to HRP to a final concentration of 2 μmol/L and the mixture was incubated at 37° ° C. for 2 min with continuous stirring. Then ADP was added to a final concentration of 2 μmol/L as an inducer. The platelet aggregation rate was determined within 5 min with a two-channel platelet aggregator (CHRONO-LOG 560). Wild-type r-Sak (2 μmol/L) and physiological saltine were assayed as controls. ADP was purchased from Sigma and other reagents were of analytic grade, made in China.

Consequently, the aggregation rate of the KGD-Sak group (3.8%±1.5%, n=3) was significantly lower than that of the r-Sak group (64%±4%, n=3) and that of the physiological saline group (60%±3%, n=3), suggesting that KGD-Sak has a powerful potency to inhibit platelet aggregation induced by ADP.

m. The Thrombolytic Assay on Animals

The animal thrombolytic assay was performed with KGD-Sak prepared in the present invention, verifying that KGD-Sak retained the same thrombolytic property as that Of wild-type Sak.

Treating experimental rabbit femoral artery thrombosis with KGD-Sak: the treatment group of KGD-Sak, the treatment group of wild-type Sak and the control group of blank each consisted of 6 animals. It was indicated by arteriography that the femoral artery under the middle segment was not visible before treatment. When photography was repeated 60 minutes after i.v. injection of 0.1 mg/kg KGD-Sak, the femoral artery was filled thoroughly and the blood cycle was recovered which was consistent with the wild-type Sak group, while in the control group, the femoral artery did not appear to be filled.

Treating experimental rabbit hyphema with KGD-Sak the treatment group of KGD-Sak, the treatment group of wild-type Sak and the control group of blank each consisted of 6 animals 4 hours after intraocular injection of 10-20 μg KGD-Sak, it was observed that the hyphema clot was lysed and the red blood cells settled and formed an interface with aqueous humor. The intraocular hematocele was eliminated after 24 hours. This is consistent with the wild-type Sak group. However, the hyphema in the control group was not significantly changed.

KGD-Sak thrombolytic therapy was safe and efficient for induced by the treatment of acute myocardial infraction experimental dog coronary arterial thrombosis. The experimental group consisting of 6 animals was given KGD-Sak at 0.3 mg/kg body weight by i.v. infusion; and the control group consisting of 6 animals was given physiological saline instead of KGD-Sak by i.v. infusion. Coronary arteriography was carried out before and after dosing Before administration, it was shown that the left anterior descending branch of the coronary artery was unfilled or filled incompletely in the animals of both groups. Arteriography was performed 30 minutes after treatment. It was shown that the left anterior descending branch was refilled in the animals of the experimental group, and the animals survived. As for the control group, there was no significant change in the region filled incompletely and the animals died several hours later.

KGD-Sak thrombolytic therapy was safe and efficient the treatment of acute cerebral infarction induced by experimental pig intracranial arterbial thrombosis. The experimental group Consisting of 6 pigs was given KGD-Sak at 0.2 mg/kg body weight by i.v. infusion; and the control group consisting of 6 pigs was given physiological saline instead of KGD-Sak by i.v. infusion. Intracranial DSA arteriography was performed before and after administration. Before administration, it was shown that there were some intracranial arteries filled incompletely in the animal of both groups. Angiography was performed 30 minutes after treatment. It was shown that the intracranial arteries were refilled in the animals of the experimental group, and the animals survived. As for the control group, there was no significant change in the intracranial arteries filled incompletely and the animals died several days later.

Without further detailed description, those skilled in the art can apply the invention to the maximum in the light of the foregoing teaching. Thus, it is to be understood that the preferred specific embodiments above are intended as illustrations, but in no way to limit the scope of the invention.

All the references cited herein are incorporated by reference in their entireties.

The substantial characteristics of the invention will become apparent to those skilled in the art from the foregoing description. Moreover, various modifications and improvement of the invention may be made without departing from the spirit of the present, inventions. Such modifications and improvements are intended to fall within the scope of the appended claims.

What is claimed is:

1. A recombinant staphylokinase derivative with bifunctionality of a thrombolytic and an anticoagulant, having the amino acid sequence of SEQ ID NO: 1 or SEQ ID NO: 3.

2. The recombinant staphylokinase derivative of claim 1, characterized in that it comprises a sequence that has 15 amino acids deleted beginning at the NH$_2$-terminal of SEQ ID NO: 1 or SEQ ID NO: 3, with Ser at residue 16 being substituted by Lys.

3. The recombinant staphylokinase derivative of claim 1 comprising the amino acid sequence of SEQ ID NO: 1.

4. The recombinant staphylokinase derivative of claim 1 comprising the amino acid sequence of SEQ ID NO: 3.

* * * * *